United States Patent [19]

Bornengo et al.

[11] Patent Number: 4,724,072

[45] Date of Patent: Feb. 9, 1988

[54] COLLECTING AGENTS FOR THE SELECTIVE FLOTATION OF LEAD AND ZINC ORES

[75] Inventors: Giorgio Bornengo, Novara; Filippo M. Carlini, Vicenza; Maria A. Marabini, Frascati; Vittorio Alesse, Rome, all of Italy

[73] Assignee: Consiglio Nazionale Delle Ricerche, Rome, Italy

[21] Appl. No.: 856,994

[22] Filed: Apr. 29, 1986

[30] Foreign Application Priority Data

Apr. 30, 1985 [IT] Italy ............................... 48019 A/85

[51] Int. Cl.⁴ ...................... B03D 1/02; C07C 149/273

[52] U.S. Cl. ..................................... 209/167; 209/166; 252/61; 548/165; 548/173; 548/174

[58] Field of Search .................. 252/61; 548/165, 173, 548/174; 209/166, 167

[56] References Cited

U.S. PATENT DOCUMENTS

| | | | |
|---|---|---|---|
| 1,788,585 | 1/1931 | Ney | 548/173 |
| 1,847,664 | 3/1932 | Ney | 252/61 |
| 1,858,007 | 5/1932 | Falconer et al. | 252/61 |
| 2,499,628 | 3/1950 | Brooks | 548/173 |
| 3,974,170 | 8/1976 | Campbell et al. | 548/174 |
| 4,431,813 | 2/1984 | Handte et al. | 548/165 |

FOREIGN PATENT DOCUMENTS

| | | | |
|---|---|---|---|
| 56971 | 4/1985 | Japan | 548/174 |

*Primary Examiner*—Robert Wax
*Attorney, Agent, or Firm*—Pollock, Vande Sande & Priddy

[57] ABSTRACT

Organic ionic collecting agents for the selective flotation of lead and zinc ores, said agents having the following general formula:

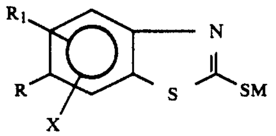

(I)

wherein the symbols have the following meanings:

R represents an alkoxyl group having from 3 to 12 carbon atoms;

$R_1$ represents H, a linear or branched chain alkyl group, an alkoxyl or hydroxyalkyl group containing up to 12 carbon atoms;

X represents H, Cl, Br, I, F, CN, $CONH_2$, $NO_2$, $SO_2NH_2$;

M represents H, Na, K, Li, Cs.

4 Claims, No Drawings

COLLECTING AGENTS FOR THE SELECTIVE FLOTATION OF LEAD AND ZINC ORES

DISCLOSURE OF THE INVENTION

The present invention relates to organic ionic collecting agents for the selective flotation of lead and zinc metal ores.

As is well known in the prior art, collecting agents known or employed at the present time can be classified into two categories: the ionic and the non ionic collecting agents. The employment of neutral or oil collecting agents is generally limited to the flotation of nonpolar minerals on which said agents become adsorbed by forces of a physical type or van der Waals forces, whereas the ionizable chemical collecting agents are employed for all other mineral species on whose surfaces said agents become adsorbed by bonds substantially of a chemical type. Chemical absorption is indeed more selective than physical adsorption, but it is to be observed that ionic collecting agents are also active towards some well determined mineral classes (as for instance sulfides), but said ionic agents do not display any selective capability towards a single mineral species.

Thus, it is necessary to employ some modified compounds in order to carry out the flotation of a given mineral from a mixture of minerals belonging to a given class, said modifiers making the collecting agent action much more specific, as is well known.

However, the use of such reagents brings about considerable drawbacks quite often and it does not give the desired result each time, especially when such reagents are employed for minerals of a complex chemical composition and whose surface properties are not sufficiently known.

Thus, it is clear that the possibility of employing collecting agents capable of bonding with some determined minerals in a selective way would be very useful. Such possibility implies the presence within the structures of said collecting agents of active groups having a specific affinity towards some specific cations which are characteristic of the mineral surface.

Assuming that a close correlation exists among the phenomena occurring in solution which involve actual chemical reactions and the phenomena occurring on the mineral surfaces, the possibility has been advanced according to the present invention of exploiting for the flotation process some ionic organic reagents which at the present time are considered with an increasing interest in analytical chemistry, because of their features of specific or highly selective action towards some given inorganic ions, and particularly towards some metal ions.

Such reagents are well known in analytical chemistry as "chelating agents". They are organic compounds which are capable of linking to some specific metal ions at a number of sites of their molecules with the formation of one or more rings that give the compound a very high stability.

Very rare and general information is available as regards the employment of such reagents in flotation processes, and such information comes in most cases from technical papers or operations of many years ago. For instance, Gutzeit employed chelating agents in the anionic flotation of the oxidized minerals of iron as sequestering agents for the heavy metal ions in order to prevent quartz from being floated. On such bases, the present invention solves the problem of obtaining the hydrophobic character of the mineral particles to be floated advantageously by introducing hydrocarbon groups as functional groups into some classes of organic chelating agents to be exploited as collecting agents for flotation processes.

Accordingly, it is an object of the present invention to supply a class of ionic organic collecting agents which are selective in the flotation of lead and zinc ores, and have the following general formula:

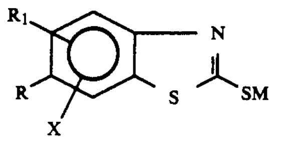

(I)

wherein the symbols employed have the following meanings:

- R represents an alkoxyl group having from 3 to 12 carbon atoms;
- $R_1$ represents H, a linear or branched chain alkyl group, an alkoxyl or hydroxyalkyl group containing up to 12 carbon atoms;
- X represents H, Cl, Br, I, F, CN, $CONH_2$, $NO_2$, $SO_2NH_2$,
- M represents H, Na, K, Li, Cs.

The collecting agents of the present invention are preferably suitable for the flotation of cerussite, galena, smithsonite, hemimorphite, zinc blende and the like.

The class consisting of the selective collecting agents for flotation corresponding to the general formula (I) which are the object of the present invention has not been disclosed up to the present time, even though some compounds are known which are derivatives of the 2-mercaptobenzothiazole, which have a limited application as reagents for analysis or as accelerating agents for vulcanization of rubber. Moreover, no information is available at the present time as to the employment of compounds corresponding to the general formula (I) in the field of the selective collecting agents for the flotation of lead and zinc ores.

The possibility of synthesizing ionic collecting agents of notable characteristics for the selective flotation of lead and zinc ores such as those of formula (I) obtained according to the present invention is quite unforeseeable for those skilled in the art, as is evident from the facts mentioned above.

This and other objects of the present invention can be obtained by means of the compounds of the general formula (I).

As an illustration, said compounds can be obtained through a process in which a derivative of the formula:

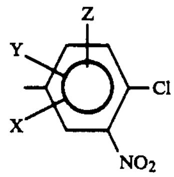

(II)

wherein X has the same meaning as given above, Y and Z, which can be the same or different from each other represent H, —OH, —CHO, is reacted with a linear or branched alkyl halide so as to obtain a compound of the formula:

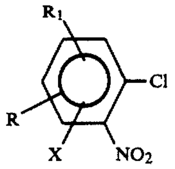

(III)

wherein X, R and $R_1$ have the same meaning as given above, which compound is then treated with sodium polysulfide so as to transform the same into the ortho-amino-mercapto-derivative and carbon disulfide in order to transform it by cyclization into a 2-mercaptobenzothiazole with the substituent groups X, $R_1$ and $R_2$ as shown in the general formula (I).

It is to be observed that the collecting agents for flotation processes which are taken into consideration in the process according to the present invention, are only those capable of forming with metals water insoluble compounds. In said compounds, the metal ion is bonded to the organic molecule through ionic bonds as well as through a donor type bond; the association between the metal and the collecting agent occurs so that the coordination number and the electric charge of the metal are balanced respectively by the sum of the donor groups and of the ionic charges of the collecting agent with which the metal combines.

Thus, it was made clear according to the present invention that the properties of the reagents in question are better with respect to those of common collecting agents, such properties differing from those of the latter above all as regards the high specific character towards metal ions, and as regards the structural differences of their nonpolar portions.

Hence the present invention allows to obtain improved organic ionic collecting agents for the selective flotation of metal minerals, particularly of structurally complex minerals, for instance lead and zinc minerals, which give a number of difficulties in the selective flotation.

Such collecting agents were shown to be of a high importance from the practical as well as from the economic viewpoint.

More particularly, the choice of a collecting agent for each mineral type was determined by its capability of giving chelation compounds which are insoluble with cations making part of the composition of the mineral itself.

Experimental tests were carried out in order to obtain all data inherent to the present invention according to the principles of analytical chemistry, so that the pH values and the collecting agent concentration were found at which the flotation process of said lead and zinc ores gives satisfying results.

Next the changes were studied for each mineral in the recovery within the full range of the pH values, keeping the concentrations of the collecting agents fixed at the values obtained in the experimental tests mentioned above.

In such a way that optimal pH value for the flotation operations was determined with a very high precision.

Flotation condition were set forth for all minerals under which a quite full recovery was obtained in the presence of the collecting agent.

Such conditions are similar to those in which the quantitative precipitation is carried out of the cation in question according to the principles of analytical chemistry.

All that shows again the possibility of transposing the principles that govern the reactions in solution to the phenomena occurring on surfaces, and in addition all that confirms the validity of the hypothesis that forms the basis of the procedure according to the present invention.

Again according to the present invention it was also found that, when a linear or branched alkyl hydrophobic chain, an alkoxy or a hydroxyalkyl group containing a number of carbon atoms up to 12, are introduced into an aromatic molecule containing two chelating functions (—N= and Sm) at a "beta" position, with a salt-forming chelating activity and some further substituent groups, said aromatic molecule gives by itself the features that are separately given by the chelating agents and by the oil.

This invention will be disclosed in the following by means of application and preparation examples of said collecting agents, said examples being given merely as illustrative examples and not for limitative purposes of the spirit and scope of the present invention.

The general conditions for flotation tests employed and illustrated in the examples given below are the following:

Grinding: a sample weighing 900 g was taken from a rough ore coming from Caitas (Sardinia) and crushed and granulated down to a size lower than 3 mm, then said sample was placed into a laboratory rod mill together with 900 g of tap water, and the whole was ground for a time sufficient to obtain the reduction of 90% of the sample to sizes lower than 100 microns, and finally extracted and diluted with 3 liters of water.

Cyclone treatment: the sample from the grinding step was treated within a Raffinot microcyclone with a vertex hole of 1.5 mm and under a pressure of 1 atmosphere. That operation eliminated a fraction of the ore corresponding to about 15% of the total sample, with particle sizes whose 90% was lower than 12 microns. The fraction whose 80% was of particle sizes between 10 and 100 microns was treated by flotation; material balances were set forth by reference to such fraction.

Flotation: the sample free from the fines and coming from the cyclone treatment was introduced into a 2 liters cell that made part of a Humboldt-Wedag flotation apparatus and stirred by means of the rotor of said apparatus. While keeping the air inlet valve closed, one of the collecting agents under test was added and allowed to condition for two minutes, and thereafter a reagent was introduced for foam production (a frothing agent). At the end of the conditioning period, during which the pH value was continuously controlled, the air suction valve was opened and the speed of the rotor was adjusted at 1,200 revolutions/minute, so as to obtain a foam carrying the ore which was removed manually by means of a small shovel till exhaustion of said foam, or, in case of persistency of the same, till the absence of the ore in the foam itself. The product of this step has been called in the examples "the product". The ore part remaining within the flotation cell was called "the waste".

Reactants: the collecting agents in question, added as 2% water solutions, unless specified otherwise.

Reactant proportions: the proportions of the reagents are given as g/tonne (i.e., g of the reactive agent per tonne of the solid).

EXAMPLE 1

The preparation of a collecting agent for flotation of the formula (a)

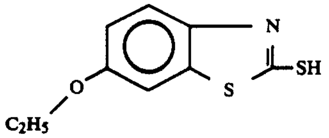

by synthesis according to R. F. Dumbrook.

60.6 parts of sulfur and 200 parts of water were added to 228 parts of sodium sulfide ($Na_2S.9H_2O$). The mixture is stirred and heated till complete dissolution. 6.5 parts of 5-ethoxy-2-nitrochlorobenzene and 48 parts of carbon disulfide are then added to the polysulfide solution. The solution is heated to 80°-85° C. for 4 hours (the reaction course is checked by thin layer chromatography).

When the reaction is over, the excess carbon disulfide is removed by distillation and the mass reacted is diluted with water till a volume of 1 l. This volume is cooled down to 20° C. and then the product (6-ethoxy-2-mercaptobenzothiazole) is precipitated with 1/1 diluted hydrochloric acid.

After filtration the product is purified by dissolving the same in a solution containing 800 parts of water and 20 parts of sodium hydroxide.

After filtration the product is dried in a vacuum oven at 45° C.

4.8 parts of the dried product are obtained.

EXAMPLE 2

Preparation of the collecting agent for flotation of the formula:

(b)

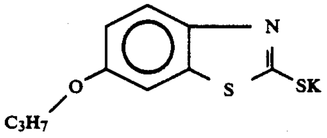

7.62 Parts of sodium sulfocyanide and 40 parts of glacial acetic acid are added to 5.6 parts of para-propoxyaniline. 12.1 parts of cupric chloride dissolved in 25 parts of ethanol are dropped into this mixture at room temperature and with stirring, then the mixture is heated up to 70° C. for 90 minutes and thereafter up to 100° C. for 30 minutes. 80 parts of diluted hydrochloric acid are introduced dropwise into said mixture while it is hot and under stirring. After filtering, the solution is treated at 40° C. with 0.4 parts of activated carbon. After filtration the intermediate product is precipitated by adding about 60 parts of sodium carbonate. The filtered material is refluxed for 6 hours with 100 parts of a 50% potassium hydroxide solution. The mixture is cooled down to room temperature and 15 parts of carbon disulfide are added dropwise to the same while stirring. Then the mixture is heated up to 70° C. for 2 hours. After filtering and drying, 3 parts are obtained of the potassium salt of the 2-mercapto-6-propoxybenzothiazole.

The yield, with respect to para-propoxyaniline is 45%.

EXAMPLE 3

Preparation of a collecting agent for flotation of the formula:

(c)

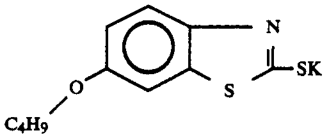

6 Parts of para-butoxyaniline are added to 30 parts of sulfur monochloride. The mixture is first stirred at room temperature for 3 hours and then at 70° C. for 2 hours.

The excess sulfur monochloride is distilled under vacuum, and thereafter the addition is performed of 100 parts of water, 50 parts of ethanol, 12 parts of sodium hydroxide and 5 parts of sodium hydrosulfite. The mixture is first stirred at room temperature for 3 hours and then at 50° C. for 1 hour. 15 parts of carbon disulfide is added dropwise at room temperature portionwise. The mixture is heated up to 70° C. for 1 hour. 2.9 parts is obtained of the potassium salt of 2-mercapto-6-butoxybenzothiazole after filtration and drying.

The yield with respect to para-butoxyaniline is 40%.

Data are reported in the following as relative to the activities of the collecting agents corresponding to the formulas (a) and (b).

The collecting agent of example 1

Raw ore processed: Lead, 4.5%; zinc, 7%. Main minerals in the gangue: calcite, dolomite, quartz.

(a) The reactants:

Collecting agent: 200 + 150 + 150 g/tonne
Aerfroth 65: 6 g/tonne
pH = 7.5
Results obtained:

| | Weight % | Pb concentration, % | Pb recovery, % | Zn concentration, % | Zn recovery, % |
|---|---|---|---|---|---|
| "product" | 15.24 | 25.60 | 86.96 | 5.92 | 13.31 |
| "waste" | 84.76 | 0.69 | 13.04 | 6.93 | 86.69 |

(b) The reactants:

Collecting agent: 400 g/tonne
Aerfroth 65: 6 g/tonne
pH = 8
Results:

| | Weight % | Pb concentration, % | Pb recovery, % | Zn concentration, % | Zn recovery, % |
|---|---|---|---|---|---|
| "product" | 17.01 | 20.59 | 91.22 | 5.80 | 12.66 |
| "waste" | 82.99 | 0.41 | 8.78 | 5.58 | 87.34 |

The collecting agent of example 2.

Raw ore processed: the same as that of example 1

The reactants:

Collecting agent: 500 g/tonne
Aerfroth 65: 20 g/tonne
pH = 7.8
Results:

| | Yield % | Pb concentration, % | Pb recovery, % | Zn concentration, % | Zn recovery, % |
|---|---|---|---|---|---|
| "product" | 9.19 | 35.70 | 82.06 | 7.76 | 9.29 |

-continued

| | | | | | |
|---|---|---|---|---|---|
| | Collecting agent: 500 g/tonne<br>Aerfroth 65: 20 g/tonne<br>pH = 7.8<br>Results: | | | | |
| | Yield % | Pb concentration, % | Pb recovery, % | Zn concentration, % | Zn recovery, % |
| "waste" | 90.81 | 0.79 | 17.94 | 7.66 | 90.71 |

The present invention has been disclosed for illustrative and not for limitative purposes, according to some preferred embodiments of the same, but it is to be understood that modifications and changes can be introduced into this invention by those skilled in the art without departing from the spirit and scope of the invention for which a priority right is claimed.

We claim:

1. A process for the flotation of ores which contain lead or zinc minerals which comprises adding to a suspension of said ore an agent which has the following formula:

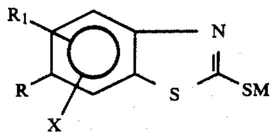

wherein:

R represents an alkoxyl group having from 3 to 12 carbon atoms;

$R_1$ represents H, a linear or branched chain alkyl group, an alkoxyl or hydroxyalkyl group containing up to 12 carbon atoms;

X represents H, Cl, Br, I, F, CN, $CONH_2$, $NO_2$ or $SO_2NH_2$; and,

M represents H, Na, K, Li or Cs.

2. The process of claim 1 wherein said agent is the potassium salt of 2-mercapto-6-butoxybenzothiazole.

3. The process of claim 1 wherein said agent is the potassium salt of 2-mercapto-propoxybenzothiazole.

4. The process of claim 1 wherein said ore contains at least one mineral selected from the group consisting of cerussite, galena, smithsonite, hemimorphite and zinc blende.

* * * * *